United States Patent [19]

Seltzman et al.

[11] Patent Number: 4,564,528
[45] Date of Patent: Jan. 14, 1986

[54] AMINOMALONYL ALANINE COMPOUNDS AND USE AS DIETARY SWEETENERS

[75] Inventors: Herbert H. Seltzman, Raleigh; Yung-Ao Hsieh, Durham, both of N.C.

[73] Assignee: Research Triangle Institute, Research Triangle Park, N.C.

[21] Appl. No.: 651,859

[22] Filed: Sep. 18, 1984

[51] Int. Cl.[4] .......................... A23L 1/236; A23L 2/38
[52] U.S. Cl. .................................... 426/548; 426/590; 260/112.5 R
[58] Field of Search ........................ 426/548; 560/169; 562/561; 260/112.5 R

[56] References Cited

U.S. PATENT DOCUMENTS

| | | |
|---|---|---|
| 29,682 | 6/1948 | Cella et al. . |
| 3,475,403 | 10/1969 | Mazur . |
| 3,492,131 | 1/1970 | Schlatter . |
| 3,920,626 | 11/1975 | Ariyoshi et al. . |
| 4,029,701 | 6/1977 | Haas et al. . |
| 4,059,706 | 11/1977 | Pischke et al. . |
| 4,411,925 | 10/1983 | Brennan et al. . |

FOREIGN PATENT DOCUMENTS 28068  8/1973  Japan .................................. 426/548

OTHER PUBLICATIONS

CA 78:111760c, 1973.
CA 67:22136j, 1967.
CA 88:165660v, 1978.
CA 79:126774e, 1973.
CA 77:102177v, 1972.
CA 87:162197t, 1977.
CA 80:46638u, 1974.

*Primary Examiner*—Raymond Jones
*Assistant Examiner*—Carolyn Paden
*Attorney, Agent, or Firm*—Cushman, Darby & Cushman

[57] ABSTRACT

Compounds having relatively long shelf lives in acidic aqueous media and which are useful as sweeteners have the formula

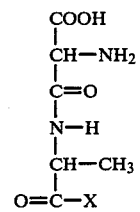

or are pharmaceutically acceptable salts thereof, wherein X is —OR or —NHR, or —NH$_2$, with R being alkyl having 3–10 carbon atoms.

7 Claims, 2 Drawing Figures

AMINOMALONYL ALANINE COMPOUNDS AND USE AS DIETARY SWEETENERS

FIELD OF THE INVENTION

This invention relates to new chemical compounds and to methods of using them as dietary sweetners. In particular the invention also relates to compounds broadly classified as aminomalonyl alanine derivatives.

BACKGROUND OF THE INVENTION

Since the introduction of saccharin as an artificial sweetener, relatively few new sweeteners have been developed. Among those that have been discovered, however, chief among them is the methyl ester of L-α-Aspartyl-L-phenylalanine, more commonly known as aspartame, disclosed in U.S. Pat. No. 3,492,131 to Schlatter. The viability of aspartame's use in non-dry applications is in serious question, however. Its recent introduction for use in soft drinks in this country was as a mixture with saccharin, the saccharin being used to maintain a sweet taste long after aspartame hydrolyzes to a non-sweet structure.

Thus, a non-toxic artificial sweetener compound comparable in sweetening ability to aspartame but which exhibits superior stability to aspartame in aqueous media would be a useful addition to the artificial sweeteners industry. Such compounds, compositions containing them, and methods of using these compounds as artificial sweeteners are the subject of the present invention.

SUMMARY OF THE INVENTION

The present invention provides compounds useful as artificial sweeteners having the following structure:

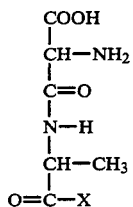

wherein X is —OR or —NHR, R being alkyl of 3–10 carbon atoms, or —NH$_2$. A preferred embodiment results when X is —OR and R is an isopropyl group, i.e. the isopropyl ester of aminomalonyl-D-alanine (herein also referred to simply as the "isopropyl ester"). Stereochemically, when synthesized the compounds of the present invention result as diasteromeric mixtures. The above formula is shown for convenience but it should be noted that the compounds will likely exist as zwitterions.

It is believed that the pharmaceutically acceptable salts, such as the tartrate, hydrochloride, and phosphate, of the compounds disclosed herein are also effective as sweeteners. Such salts can be made using typical acids and procedures for making the salts as are conventionally known and practiced in the art.

The compounds of this invention generally range in sweetness between that of sucrose and aspartame. For example, the isopropyl ester of aminomalonyl alanine is 58 times sweeter than sucrose and about half as sweet as aspartame on a weight basis. Compared to saccharin, the isopropyl ester does not possess a "metallic" aftertaste, and there are virtually no detracting side tastes.

Additionally, the compounds of this invention are believed to be non-toxic. Concerns have been raised regarding the principle metabolism products of aspartame—aspartic acid and phenylalanine. The former causes brain lesions in neonatal mice and the latter has been reported to induce grand mal-type seizures in monkeys, produce birth defects in pregnant women with phenylketonuria, induce behavioral changes, and alter brain chemistry. Saccharin itself is well known as a weak mutagen in the Ames assay, a property which is associated with carcinogenic potential.

Thus, in addition to the compounds having the structure given above, the invention also provides a method of sweetening a beverage, comprising dissolving a sufficient amount of at least one of the compounds disclosed herein to effect said sweetening.

It is therefore an object of this invention to provide an artificial sweetener.

It is further an object of this invention to provide an artificial sweetener which is relatively stable in aqueous solution.

It is further an object of this invention to provide an artificial sweetener which is non-toxic.

These and other objects and advantages of the invention will become more apparent and more readily appreciated from the following detailed description of presently preferred exemplary embodiments of the invention taken in conjunction with the accompanying FIGURE which is a diagrammatic representation of the synthesis of DL-α-aminomalonyl-D-alanine isopropyl ester. The lower case letter designations refer to the following:

a. Benzyl chloroformate (Z—Cl), NaHCO$_3$
b. NaOH, aq. EtOH
c. DBU, Benzyl bromide
d. tetramethylguanidine (TMG), aq. THF
e. DCC, HOBt, THF, D-alanine isopropyl ester (6)
f. 10% Pd/C, H$_2$, MeOH.

DETAILED DISCUSSION

The synthesis of compounds within the scope of this invention will be described using the preferred isopropyl ester as an example, although this description is strictly for purposes of illustration, not limitation.

I. Synthesis of DL-α-aminomalonyl-D-alanine isopropyl ester

Figure 1:
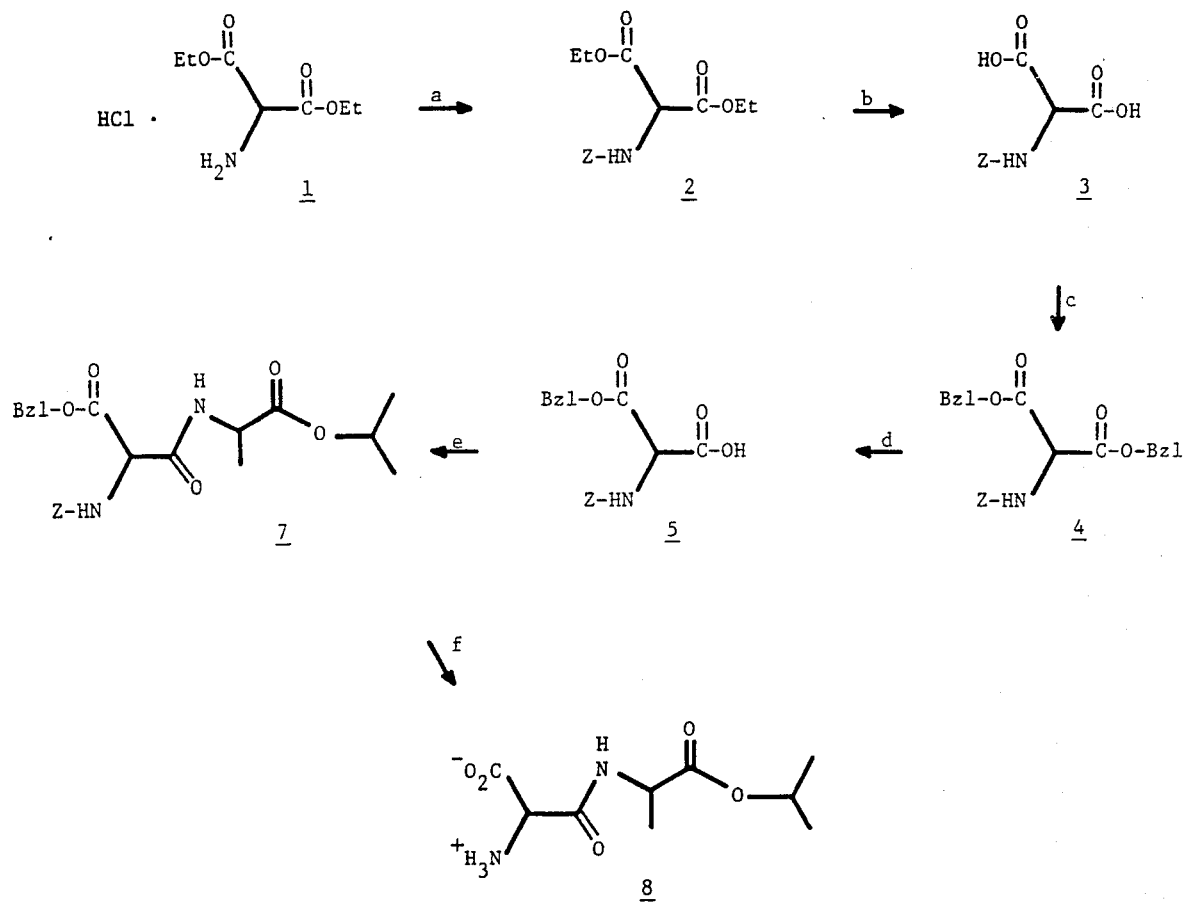
FIG. 1 is a flow chart illustrating the synthesis of DL-α-aminomalonyl-D-alanine isopropylester.

As an overview of the synthetic methods employed, the synthesis of DL-α-aminomalonyl-D-alanine isopropyl ester is shown in FIG. 1 and is now briefly summarized. Commercially available aminomalonic acid diethyl ester hydrochloride 1 was treated with Z—Cl (Z is an abbreviation for a benzyloxycarbonyl group) and NaHCO$_3$ to afford the N-protected Z-Ama-(OEt)$_2$ 2 (Ama=aminomalonyl group; Et=ethyl). Saponification provided the free acid 3. Treatment with excess benzyl bromide and 1,8-diazabicyclo[5.4.0]undec-7-ene (DBU) yielded the diester 4 which upon partial saponification provided the monobenzyl ester 5.

Coupling of 5 with D-alanine isopropyl ester 6 to afford the protected dipeptide 7 was achieved by standard dicyclohexylcarbodiimide (DCC) mediated procedures employing either hydroxybenzotriazole (HOBt) or N-hydroxysuccinimide (HOSu) as catalysts. The yields with either catalyst were comparable (70–80%), with the latter allowing easier removal of the reaction solvent (THF vs DMF) required for solubility reasons.

The final step in the sequence, removal of the benzyloxycarbonyl (Z) and benzyl (Bzl) moieties by hydrogenolysis over 10% Pd on carbon in methanol was followed by recrystallization from methanol to afford DL-α-aminomalonyl-D-alanine isopropyl ester.

Intermediates 2, 4, 5, and 6 are known compounds. It is believed the preparation of 4 may be novel. The conversion of 4 to 5 using tetramethylguanidine is also believed to be novel.

Detailed procedural steps may be described as follows.

N-Benzyloxycarbonyl-α-aminomalonic Acid Diethyl Ester (2)

This compound was prepared according to the procedure of M. Fujino et al, Chem. Pharm. Bull. Japan, 24 (9), 2112 (1976), in which it was reported as an oil. The present inventors crystallized the crude oil from ether-petroleum ether in a dry ice-acetone bath, with scratching, to yield 5.13 g (83%); mp 37°–38° C.; 60 MHz nmr(CDCl$_3$, ppm) 1.25 (6H, t, J=7 Hz, CH$_3$CH$_2$—), 4.20 (4H, q, J=7 Hz, CH$_3$CH$_2$—), 5.03 (2H, s, ArCH$_2$—), 5.66 (1H, broad s, amide H), 7.23 (5H, s, ArH$_5$).

N-Benzyloxycarbonyl-α-aminomalonic Acid (3)

Compound 2 (3.49 mmol, 1.08 g) was dissolved in 3 mL 95% ethanol and treated with 3.49 mL 2N NaOH. The clear, colorless solution was left at room temperature for 19 h until no starting material could be detected by tlc on silica gel (benzene:ethyl acetate, 4:1). Ethanol was evaporated under reduced pressure at room temperature. The aqueous solution was washed once with ether and then acidified with concentrated HCl to pH 2.5. The milky solution was extracted with ethyl acetate (3x). The pooled extract was washed with brine, drived over anhydrous Na$_2$SO$_4$ and evaporated to dryness. The product was crystallized from ether to yield 0.852 g of compound 3; mp 144°–145° C.; homogenious by tlc on silica gel (CHCl$_3$:methanol:acetic acid, 5:13:0.1); 250 MHz nmr (acetone-d$_6$, ppm) 5.00 (1H, d, J=8 Hz, α-H), 5.10 (2H, s, ArCH$_2$—), 6.84 (1H, d, J=8 Hz, amide H), 7.36 (5H, m, ArH$_5$). In a 60 MHz spectrum run in low water content acetone, a 9.7 ppm (2H, broad s, exchangeable with D$_2$O) was also observed.

N-Benzyloxycarbonyl-DL-α-aminomalonic Acid Monobenzyl Ester (5)

Compound 3 (4.94 mmol, 1.25 g) was dissolved in a mixture of 8 mL tetrahydrofuran (THF) and 8 mL CH$_3$CN. Benzyl bromide (9.88 mmol, 1.18 mL) and 1,8-diazabicyclo[5.4.0]undec-7-ene (DBU)) (N. Ono et al., Bull. Chem. Soc, Japan, 51, 2401, 1978; C. G. Rao, Org. Prep. Proc. Int., 12, 225, 1980) (9.88 mmol, 1.48 mL) were added. The clear, colorless solution was left at room temperature overnight. The solution was concentrated under reduced pressure to half of the original volume. The product was precipitated by addition of water. The white crystalline material was collected by filtration, dried and triturated with petroleum ether to yield compound 4; 1.72 g (80%); mp 109°–110° C.; 250 MHz nmr (CDCl$_3$, ppm), 5.11, 5.16, 5.2 (7H, s, s, m, 3 ArCH$_2$— and α-H), 5.82 (1H, d, J=8 Hz, NH), 7.30 (15H, m, 3 ArH$_5$).

Z-Ama(OBzl)$_2$ (1.78 g, 4 mmol) was dissolved in 18 mL THF. TMG (0.5 mL, 4 mmol, freshly distilled) in H$_2$O was added. The clear colorless solution gave a pH of 12.5–13.5 (pH hydrion paper). After 3 h at room temperature the pH went down to 8.5. The solution was evaporated under reduced pressure to remove THF. The cloudy solution was diluted with more water and extracted with ether. The aqueous phase was acidified to pH 2 with concentrated HCl. The cloudly aqueous phase was extracted with EtOAc (3x). The pooled EtOAc extract was washed with H$_2$O, dried over Na$_2$SO$_4$ and evaporated to dryness to give a white solid. The crude product was recrystallized from MeOH—H$_2$O. Yield: 1.17 g (86%), m.p. 118°–120° C., tlc on silica gel [CHCl$_3$:MeOH:HOAc=9:1:0.2] indicated the absence of 3 and 4. 250 MHz NMR (acetone-d$_6$, ppm). 5.06 (1H, d, partially overlapped with 5.1 peak, α-H), 5.1 (2H, s, ArCH$_2$—), 5.24 (2H, s, ArCH$_2$'—), 7.0 (1H, broad s, amide H), 7.35 (10H, m, 2 ArH$_5$).

N-Benzyloxycarbonyl-DL-aminomalonyl-(benzyl ester)-D-alanine Isopropyl Ester (7)

N-Benzyloxycarbonyl-DL-α-aminomalonic acid monobenzyl ester 5 (0.156 g, 0.434 mmol) was dissolved in 1.5 mL DMF. The solution was cooled to −15° to −20° and then treated with DCC (94 mg, 0.455 mmol) and 1-hydroxybenzotriazole hydrate (62 mg, 0.46 mmol). The reaction mixture was stirred at −15° to −20° for 1.5 hr, at 0° for 1 hr and 8 hr at room temperature. The reaction mixture was filtered to remove DCU and the filtrate was evaporated to dryness under high vacuum. The oily residue was taken up in EtOAc and the cloudy EtOAc solution was filtered. The EtOAc filtrate was then washed with 0.1N HCl (3x), H$_2$O (3x), 0.1N NaOH (3x), H$_2$O (3x), dried over anhydrous Na$_2$SO$_4$ and evaporated to dryness to give a clear oil. TLC on silica gel (benzene:EtOAc=4:1 and toluene:EtOAc=9:1) each indicated 3 spots; yield 0.187 g (91%). The crude material (0.167 g) was dissolved in CHCl$_3$, mixed with approximately 0.2 g of silica gel and loaded on a 12 g silica gel column in toluene. The crude product was then chromatographed by gradient elution with toluene to toluene:EtOAc=8:1. The major fraction (0.124 g) was identified by NMR as the desired product. The product was dissolved in a minimum amount of warm EtOAc; the solution was then diluted with an equal volume of ether and refrigerated. A while solid was obtained: mp 125°–130°, 250 MHz NMR (CDCl$_3$, ppm), 1.23 (m, 7.5H, (CH$_3$)$_2$—CHO— overlapping with β-CH$_3$ of Ala of one of the 2 diastereomers), 1.37 (d, 1.5H, J=6.98 Hz, β-CH$_3$ of Ala of the second diastereomer, 4.45 (m, 1H, α-H of Ala), 5.00 (m, 1H, α-H of isopropyl), 5.12 (s, 2H, Ar—CH$_2$—), 5.18–5.34 (m, 3H, Ar-CH$_2$-O— of the benzyl ester overlapping with α-H of Ama), 7.33 (s, 10H, 2 ArH$_5$).

A 30 mmole scale preparation following the above procedure through the extraction step afforded the crude product which was crystallized from 2-propanol to give 8.91 g of tlc homogeneous 7. Another 2.17 g (total yield 81%) of 7 was obtained from the mother liquor by the above column chromatographic procedure.

Anal. Calcd for $C_{24}H_{28}N_2O_7$: C, 63.46; H, 6.18; N, 6.14; Found: C, 63.15; H, 6.04; N, 6.06.

DL-α-Aminomalonyl-D-Alanine Isopropyl Ester (8)

N-Benzyloxycarbonyl-DL-α-aminomalonyl-(benzyl ester)-D-alanine isopropyl ester 7 (1.16 g, 2.53 mmol) was hydrogenated at room temperature in 100 mL MeOH over 0.573 g of 10% Pd/C at 40 psi in a Parr apparatus for 1 hr. The solution was then filtered through a Celite pad to remove the catalyst; the filtrate was concentrated under reduced pressure and the free dipeptides were precipitated from the solution by addition of ether. The crude product was recrystallized from MeOH. Yield 0.411 g (60%), mp 102°–104°, 250 MHz NMR (CD$_3$OD, ppm) 1.25 (m, 6H, (CH$_3$)$_2$CHO—), 1.41 (2d, 3H, β-CH$_3$ of Ala), 4.38 (2q, 1H, α-H of Ala), 4.99 (m, 1H, α-H of isopropyl).

Anal. Calcd for $C_9H_{16}N_2O_5$: C, 46.55; H, 6.95; N, 12.06; Found C, 46.53; H, 6.95; N, 12.11.

II. Taste Test

Figure 2:
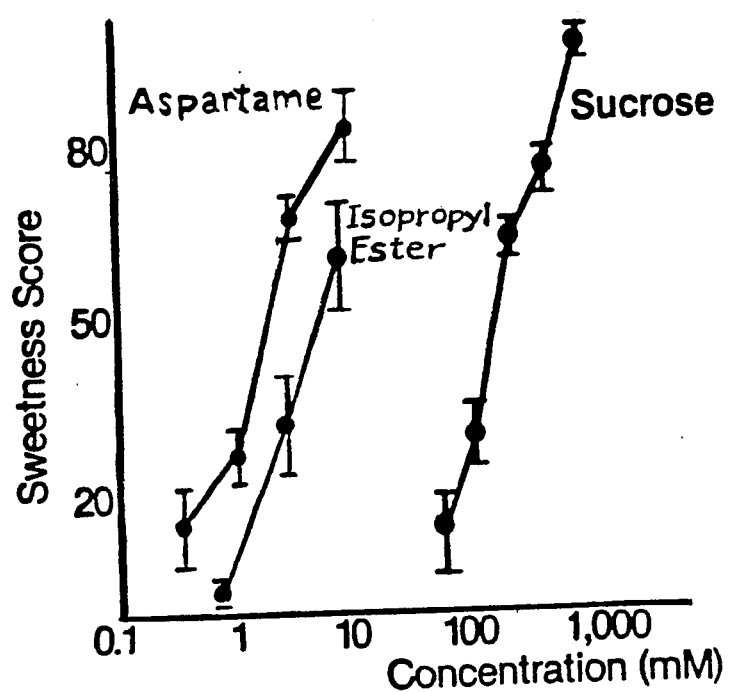
FIG. 2 is a graphical comparison of the sweetness potency of the isopropyl ester with sucrose and aspartame. Each data point represents the mean±SEM.

Following established methods a taste panel was set up and trained. The compound was tasted at concentrations of 0.021, 0.07 and 0.21% w/v (0.86, 3.0 and 9.0 mM) versus aspartame concentrations of 0.01, 0.03, 0.1 and 0.3% w/v (0.34, 1.0, 3.4 and 10 mM) and sucrose 2, 4, 9, 18 and 36% w/v (62, 125, 250, 500 and 1000 mM). The normalized averaged results for the isopropyl ester, sucrose and aspartame are given in Table 1 and shown graphically in FIG. 2.

Both the compound and aspartame solutions were rated as sweet and pleasant by the taste panel. If it is assumed that relative potency can be expressed as a ratio of reciprocal concentrations required for a score of 50 on the sweetness scale, then based on sucrose=1.0, the sweetness potency of aspartame would be 126 and that of the preferred isopropyl ester would be 58 on a weight scale. On a molar scale the relative potencies would be 1, 110 and 40, respectively.

Since the potency response lines are approximately parallel, the above potency comparison method appears reasonable and (within the limitations of a single panel test) it may be concluded that aspartame has about twice the potency of the isopropyl ester. Since the isopropyl ester, as synthesized, consists of a diasteroisomeric pair, the potency of the active component may approximate that of aspartame, however.

TABLE 1

Taste Panel Results
Average Scores for Standard and Test Compounds[1]
Test Series: 4   Test Date: December 8, 1981

| Compound | Concentration (Millimolar) | Sweet? | Bitter? | Salty? | Off Taste? | After Taste? | Pleasant? |
|---|---|---|---|---|---|---|---|
| Aspartame | 0.3392 | 15 | 0 | 1 | 1 | 1 | 4 |
| | | (7) | (0) | (1) | (1) | (1) | (2) |
| | 1.0194 | 27 | 0 | 3 | 4 | 2 | 15 |
| | | (5) | (0) | (3) | (3) | (1) | (8) |
| | 3.3979 | 68 | 4 | 2 | 2 | 26 | 26 |
| | | (4) | (3) | (1) | (2) | (7) | (18) |
| | 10.1837 | 83 | 0 | 1 | 4 | 34 | 8 |
| | | (6) | (0) | (1) | (4) | (14) | (18) |
| Sucrose | 62.0000 | 13 | 3 | 0 | 4 | 0 | −4 |
| | | (7) | (3) | (0) | (4) | (0) | (8) |
| | 125.0000 | 30 | 2 | 8 | 4 | 5 | 18 |
| | | (5) | (1) | (5) | (3) | (2) | (9) |
| | 250.0000 | 64 | 0 | 1 | 0 | 0 | 49 |
| | | (3) | (0) | (1) | (0) | (0) | (8) |
| | 500.0000 | 75 | 6 | 12 | 5 | 7 | 32 |
| | | (4) | (5) | (9) | (3) | (3) | (11) |
| | 1000.0000 | 97 | 0 | 1 | 0 | 30 | 26 |
| | | (2) | (0) | (1) | (0) | (13) | (20) |
| Isopropyl Ester | 0.8621 | 4 | 7 | 21 | 13 | 4 | −11 |
| | | (2) | (7) | (21) | (9) | (4) | (8) |
| | 3.0172 | 32 | 3 | 5 | 2 | 6 | 13 |
| | | (8) | (3) | (5) | (2) | (4) | (8) |
| | 9.0517 | 61 | 1 | 3 | 3 | 4 | 34 |
| | | (9) | (1) | (3) | (2) | (3) | (13) |

[1]The scores have been normalized to 100 and averaged. The numbers in parentheses are standard error values.

III. Stability Studies

The isopropyl ester was examined for stability in aqueous solution at various pHs. Solutions (1%) were prepared in 0.05M phosphate buffers adjusted to pH 7.4 and pH 3.5 and in distilled water. Storage at ambient temperature over 36 days was monitored by hplc analysis (Waters radial-pak A reverse phase C-8 column, 25% CH$_3$CN—H$_2$O—0.05% TFA eluant, 210 nm U.V. detection). Aspartame was examined similarly as a standard. Generally, stability was greatest at pH 3.5, good in water, and poorest at pH 7.4.

In pH 3.5 buffer the isopropyl ester showed virtually no change in 36 days while aspartame was about 50–60% degraded to more and less polar products. In water the isopropyl ester was 30–40% degraded by day 36 and aspartame was about 50% degraded. In pH 7.4 buffer the isopropyl ester was about 70% degraded by day 36. Aspartame was completely hydrolyzed in pH 7.4 buffer by day 9. The significantly greater stability of the isopropyl ester versus aspartame in pH 3.5 buffer is especially encouraging as regards its potential use in comparably acidic soft drinks.

IV. Ames/Salmonella Mutagenicity Assay

The isopropyl ester was tested for mutagenicity in five test strains each at five dose levels (3,000, 300, 30, 3, 0.3 μg/plate) with and without S9 metabolic activation and for toxicity at the two highest dose levels (with and without S9). Triplicate plates were used for all dose levels. The compound showed no mutagenic potential or toxicity for any of the tests. Positive controls and spontaneous background revertants were within acceptable ranges.

VI. Acute Toxicity Testing in Swiss Male Mice

The isopropyl ester was administered to mice on two different occasions. In the first toxicity study the compound was given as an aqueous solution at an oral dose of 100 mg/kg. On day 0, mice were weighed and the ester and two solvent controls were administered orally to groups of six mice each. Two hours after sample administration the food was returned. The mice were examined the entire first day for symptoms of toxicity; none were observed. There was no excessive eating or drinking during the study.

On each succeeding day, the mice were examined three times a day for the first week, twice a day for the second week. No behavioral or pharmacological effects were observed. On day 14, a gross necropsy was performed on each mouse and no toxic effects were detected.

The results of this acute whole animal toxicity study indicated no toxic effects under the conditions tested. The toxicological parameters were all negative. The weights of all test animals during the 14-day study were normal.

To further test the safety of the isopropyl ester, a second acute toxicity study was carried out at a dose of 300 mg/kg in an aqueous solution. As in the first study, no toxicity was observed and gross necropsy showed no toxic effects. Weights of the animals were normal.

For biochemical testing of serum samples, blood samples were collected from the tail vein. This procedure virtually eliminated hemolyzed samples. Neither elevated alanine aminotransferase (ALT) activity nor elevated serum urea nitrogen was detected in post-study sampled from the 100 mg/kg dose.

Therefore the isopropyl ester appears to meet biochemical acceptance criteria.

For the second toxicity test, carried out at a 300 mg/kg dose of isopropyl ester, none of the post-study samples contained elevated ALT activity or elevated serum urea nitrogen.

The isopropyl ester thus also appears to meet biochemical acceptance criteria at the 300 mg/kg dose.

Although only a few exemplary embodiments of this invention have been described above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. Aminomalonyl-D-alanine derivatives having the formula:

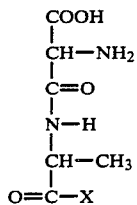

and pharmaceutically acceptable salts thereof, wherein X is —OR with R being alkyl of from 3 to 10 carbon atoms.

2. The derivative of claim 1, wherein R is isopropyl.

3. A composition of matter comprising the combination of at least one aminomalonyl-D-alanine derivative having the formula:

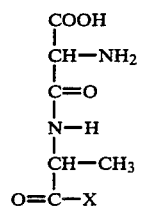

or pharmaceutically acceptable salts thereof, wherein X is —OR with R being alkyl of from 3 to 10 carbon atoms, dissolved in an aqueous medium.

4. The composition of claim 3, wherein R is isopropyl.

5. The composition of claim 3, wherein said aqeuous medium is a beverage.

6. A method of sweetening a beverage, comprising dissolving therein at least one aminomalonyl-D-alanine derivative having the formula:

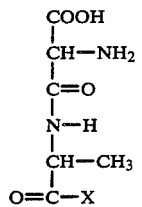

or pharmaceutically acceptable salts thereof, wherein X is —OR with R being alkyl of from 3 to 10 carbon atoms, said at least one compound being dissolved in an amount sufficient to effect said sweetening.

7. The method of claim 6, wherein R is isopropyl.

* * * * *